United States Patent [19]

Nosticzius et al.

[11] Patent Number: 4,968,484
[45] Date of Patent: Nov. 6, 1990

[54] ANNULAR GEL REACTOR FOR CHEMICAL PATTERN FORMATION

[75] Inventors: Zoltan Nosticzius, Budapest, Hungary; Werner Horsthemke, Austin, Tex.; William D. McCormick, Austin, Tex.; Harry L. Swinney, Austin, Tex.; Wing Y. Tam, Austin, Tex.

[73] Assignee: Board of Regents, The University of Texas System, Austin, Tex.

[21] Appl. No.: 189,929

[22] Filed: May 3, 1988

[51] Int. Cl.$^5$ ............................................. G01N 31/00
[52] U.S. Cl. .................................... 422/68.1; 422/58; 436/165; 436/515; 435/283; 435/287
[58] Field of Search .................... 422/68, 58; 436/515, 436/165; 435/283, 287

[56] References Cited

U.S. PATENT DOCUMENTS 3,069,340 12/1962 Mindick et al. ..................... 204/180
4,092,117 5/1978 Byrne ................................. 23/230 R
4,308,351 12/1981 Leighton et al. ................... 435/284

OTHER PUBLICATIONS

Vidal et al. "Experimental Statistical Study of Target Patterns Produced by An Oscillating Belousov-Zhabotinsky Reaction" J. Physique, 47, pp. 1999-2009, Nov., 1986.

Noszticzius et al. "Sustained Chemical Waves in an Annular Gel Reactor: A Chemical Pinwheel" Nature, 329, pp. 619, 620, Oct. 15, 1987.

J. Ross et al. "Chemical Waves" Science, 240, pp. 460-465, Apr., 1988.

Primary Examiner—Robert J. Warden
Assistant Examiner—Lynn M. Kummert
Attorney, Agent, or Firm—Renner, Kenner, Greive, Bobak, Taylor and Weber

[57] ABSTRACT

The present invention is directed to an annular gel reactor suitable for the production and observation of spatiotemporal patterns created during a chemical reaction. The apparatus comprises a vessel having at least a first and second chamber separated one from the other by an annular polymer gel layer (or other fine porous medium) which is inert to the materials to be reacted but capable of allowing diffusion of the chemicals into it.

5 Claims, 1 Drawing Sheet

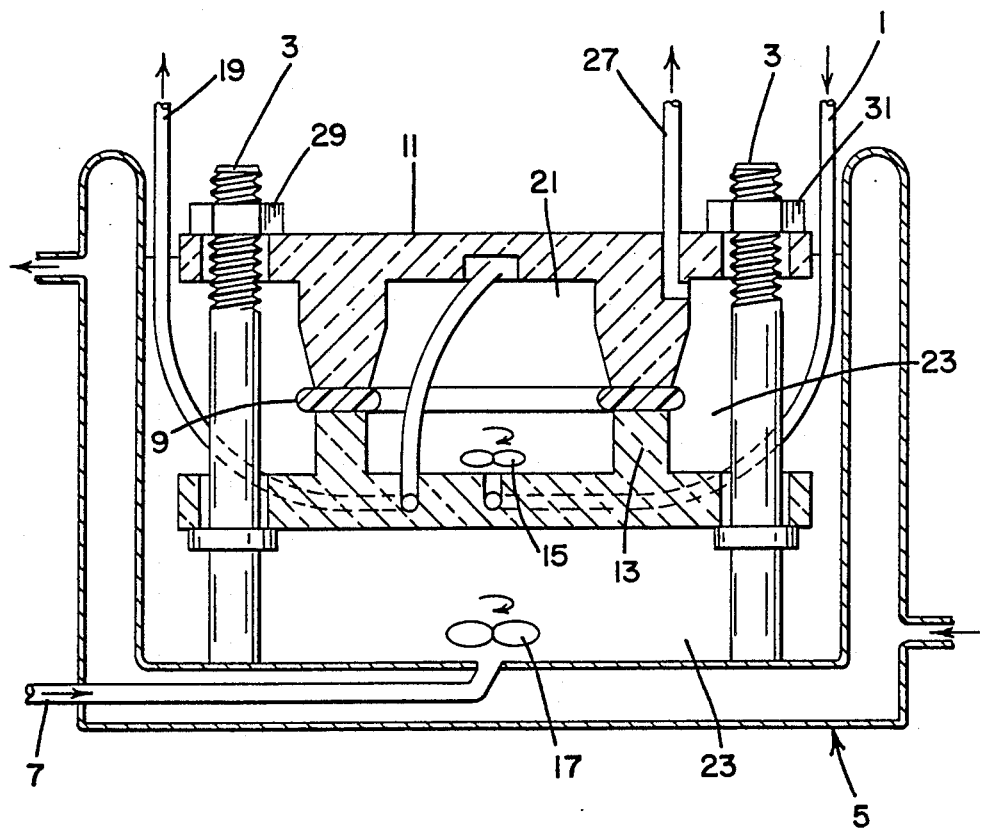

ANNULAR GEL REACTOR FOR CHEMICAL PATTERN FORMATION

BACKGROUND OF THE INVENTION

The present invention is directed to a process for generating spatiotemporal patterns in a chemical reaction and the device for producing and observing these patterns. In particular, the present invention is directed to a process and device for the creation of spatiotemporal patterns by feeding the materials into a reactor in a manner so that convective motion does not interfere with the chemical pattern achieved during the reaction. The process and reactor of the present invention has specific utility in the study of various spatial patterns of chemical reactions to understand the particular mechanism of the reaction and also as a means for concentrating highly desirable chemical intermediates in a specific area of the solution so that these chemical materials may be extracted in greater concentrations. Specifically, the process and apparatus may be utilized in biological methods whrein small amounts of highly valuable enzymes are produced and are difficult to seperate because of their low concentration.

In the discussion of the process and apparatus of the present invention, specific reference will be made to the Belousov-Zhabotinsky reaction system which has been studied for a number of years in an attempt to understand the formation of chemical spatial structures (mainly chemical waves) formed in a chemical reaction. For a detailed description of that work, see Vidal et al., "Etude . . . Oscillant", *J. Physique*, 47, pp 1999–2009, Nov. 1986, herein incorporated by reference.

Many experiments on spatial self organization in chemical systems have yeilded spiral waves and concentric ring patterns. Those experiments were conducted in closed reactors. Hence, the system evolved irreversibly and uncontrollably toward thermodynamic equilibrium. The transient nature of the spatial patterns and the lack of a well-defined controlled parameter complicates the interpretation of those experiments. About a decade ago, the CSTR (continuous flow stirred tank reactor) replaced closed reactors in experiments on well mixed oscillating chemical reactions. Subsequently a wide variety of new dynamical phenomena were discovered in the study of these oscillating chemical reactions.

The present invention is directed to an annular gel reactor which can serve as a tool for the systematic study of the spatial patterns generated in these chemical reactions. The gel in the reactor of the present invention prevents the occurrence of convective motion in the reaction. Covective motion has plagued previous studies of chemical pattern formation.

SUMMARY OF THE INVENTION

It is the primary object of the present invention to provide a novel chemical reactor used to generate and maintain spatial patterns in an on-going chemical reaction.

It is a second object of the present invention to provide a process for the generation and maintenance of spatiotemporal patterns in an on-going chemical reaction.

Additional objects and advantages of the invention will be set forth in part in the description which follows and in part will be obvious in the description or may by learned be the practice of the invention. The objects and advantages of the invention may be realized and attained by means of the instrumentalities and combinations particularly pointed out in the appended claims.

To achieve the foregoing objects and in accordance with the purpose of the present invention as embodied and broadly described herein, the reactor of the present invention comprises a vessel having a first and second chambers seperated one from the other by an annular polymer gel or other fine porous medium inert to the materials to be placed in the chambers and capable of allowing diffusion of the reacting materials. The annular gel is clamped in place by means of a transparent plate.

In a further embodiment of the presant invention the process of producing a spatial pattern in a chemical reaction comprises introducing the first chemical reactant into the first chamber of the vessel and the second reactant into the second chamber of the vessel. The first and second reactants are stirred in their respective chambers separate from one another. The reactants then diffuse into the polymer gel separating the first chamber from the second chamber and react therein creating the spatial pattern in the gel.

The advantage of the process and apparatus of the present invention is that a porous medium, in the present embodiment a polymer gel prevents any convective motion in the reacting region due to thermal and concentration gradients created by the reaction.

The accompanying drawing which is incorporated and constitutes a part of this specification illustrates a preferred embodiment of the invention and together with the description, serves to explain the principles of the invention.

BRIEF DESCRIPTION OF THE DRAWING

The FIGURE is a cross-sectional view of the aparatus of the present invention.

DETAILED DESCRIPTION OF THE INVENTION

With reference to the accompanying drawings, the process and apparatus of the present invention will now be set forth in detail.

The FIGURE is a cross-sectional view of a preferred apparatus of the present invention.

Vessel 5 contains an inner chamber 21 and an outer chamber 23 separated one from the other by polymer gel ring 9. Transparent annular support clamp 11 holding annular polymer gel 9 in position in vessel 5 is secured by support posts 3. A first chemcial reactant solution is fed into chamber 21 by means of tube 1 and a second chemical reactant solution is fed into outer chamber 23 by means of tube 7. The inner solution flows out from chamber 21 by means of tube 19 and the outer solution flows from chamber 23 by means of outlet 27. Support posts 3 are threaded posts with a transparent clamp 11 having holes for the post. Support clamp 11 is secured in place with nuts 29 and 31.

In operation, inner chamber 21 is filled with chemical reactants via tube 1 and outer chamber 23 is filled with second chemical reactants via tube 7. Inner and outer chambers 21 and 23 are each mixed using magnetic stirrers 15 and 17, respectively. The solutions in chambers 21 and 23 are completely separated one from the other. The reactants in chambers 21 and 23 diffuse through annular polymer gel 9. The reactants react in the annular gel creating a spatiotemporal chemical pattern. Since clamp 11 is formed of a clear transparent material, the waves generated in the gel ring 9 are clearly visible. The polymer gel material must be inert to the chemical reactants. A suitable polymerical material for study of the Belousov-Zhabotinsky Reaction is polyacrylamide.

The feed chemicals diffuse into the annular gel from the inside and outside boundaries. There is no hydrodynamic flow through this region. The gel prevents any convective motion which might be caused by thermal and concentration gradients created by the reaction. Therefore, the reactor can produce spatiotemporal chemical patterns without any interference from hydrodynamic processes. At specific locations in the spatiotemporal pattern, the concentration of certain chemical intermediates is orders of magnitude greater than the background concentration. Accordingly, extraction of these materials at those specific locations provides higher yeild of these materials than is normally achieved by conventional techniques.

The following example of the present invention is set forth for purposes of illustration.

EXAMPLE

The reaction studied was the Belousov-Zhabotinsky (BZ) Reaction described previously. The $H_2SO_4$ and $KBrO_3$ components of the BZ reaction were placed in chamber 23 and malonic acid with the ferroin catalyst was placed in chamber 21. The reactants then diffused through the polyacrylamide gel 9 and react. The reaction is observed through clear clamp 11. At the beginning of the experiment a red concentric front of ferroin can be seen. After 2 to 3 hours, the circular symmetry of the front starts to break and irregularities are observed. Finally, a state devolops with one or more pacemaker centers (wave sources) and with the same number of annihilation points. The number and frequency of the pacemakers varies randomly. An appropriate perturbation of these spontaneously appearing chemical waves results in stable, regular, rotating waves ("chemical pinwheels"). The system can be perturbed by two different techniques:

(i) An artificial pacemaker is created by filling a bore in the transparent clamp with a high concentration solution of $H_2SO_4$ and $KBrO_3$. This perturbant diffuses into the gel and generates a wave source. To stop the pacemaker, the bore is washed with distilled water. To set up rotating waves, the clockwise (or counterclockwise) waves are eliminated by placing a barrier close to the artificial pacemaker in the clockwise (or counterclockwise) direction. The barrier is a region in the gel where the reagents have been diluted by a slow continuous flow of distilled water through a second bore in the transparent clamp. The barrier is not perfect; every second or third wave goes through. But this still produces an overwhelming excess of counterclockwise (clockwise) waves after a while. If we remove the barrier and stop the artificial pacemaker, the production of waves is stopped and the few clockwise (counterclockwise) waves will be annihilated along with an equal number of counterclockwise (clockwise) waves. Only counterclockwise (clockwise) rotating waves remain in the annulas. The total number of rotating waves can now be changed by activating the barrier again; in this way the number of waves can be decreased. (ii) The apparatus is first covered with black paper except for a small region of the annulus and illuminated with incandescent light. The illuminated region becomes a pacemaker and a pattern devolops which has approximately the same number of clockwise and counterclockwise waves. Then the clockwise (counterclockwise) waves are covered with black paper and the counterclockwise (clockwise) waves are illuminated with an intense light source for 1 minute. This eliminates the counterclockwise (clockwise) waves and generates a chemical pinwheel.

The foregoing description of a preferred embodiment of the present invention has been presented for purposes of illustration and description. It is not intended to be exhaustive or to limit the invention to the precise form disclosed, and obviously many modifications and variations are possible in light of the above teaching. This embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A chemical reactor for producing and studying spatiotemporal patterns generated during the reaction of at least two materials comprising:
   a vessel having a first and second chamber;
   a reaction chamber comprising a porous polyacrylamide gel medium inert to the reactant materials, disposed between said first and second chambers, and secured in place by a transparent support clamp;
   said first and second chambers serving to supply the reactant materials to said reaction chamber wherein they react.

2. A chemical reactor as in claim 1, further including reactant feed means communicating with said first and second chambers; and outlet means communicating with said first and second chambers.

3. A chemical reactor for producing and studying spatiotemporal patterns generated during the reaction of at least two materials comprising:
   a vessel having a first and second chamber;
   an annular shaped reaction chamber comprising a porous gel medium inert to the reactant materials and disposed between said first and second chambers,
   said first and second chambers serving to supply the reactant materials to said reaction chamber wherein they react.

4. A chemical reactor as in claim 3, wherein said porous gel medium is secured in place in said vessel by means of a transparent support clamp.

5. A chemical reactor as in claim 3, further including reactant feed means communicating with said first and second chambers; and outlet means communicating with said first and second chambers.

* * * * *